United States Patent
Uematsu et al.

(10) Patent No.: US 10,676,690 B2
(45) Date of Patent: Jun. 9, 2020

(54) METHOD FOR RUPTURE OF ALGAE

(71) Applicant: Kao Corporation, Tokyo (JP)

(72) Inventors: Takafumi Uematsu, Wakayama (JP); Kotaku Yuasa, Wakayama (JP); Saki Hamada, Wakayama (JP); Takaaki Watanabe, Wakayama (JP)

(73) Assignee: KAO CORPORATION, Tokyo (JP)

( * ) Notice: Subject to any disclaimer, the term of this patent is extended or adjusted under 35 U.S.C. 154(b) by 342 days.

(21) Appl. No.: 15/533,827

(22) PCT Filed: Dec. 8, 2015

(86) PCT No.: PCT/JP2015/006110
§ 371 (c)(1),
(2) Date: Jun. 7, 2017

(87) PCT Pub. No.: WO2016/092828
PCT Pub. Date: Jun. 16, 2016

(65) Prior Publication Data
US 2017/0327766 A1    Nov. 16, 2017

(30) Foreign Application Priority Data
Dec. 9, 2014  (JP) ................ 2014-248539

(51) Int. Cl.
| | | |
|---|---|---|
| C11B 1/02 | (2006.01) | |
| C12P 7/64 | (2006.01) | |
| B02C 19/06 | (2006.01) | |
| C12N 1/06 | (2006.01) | |
| C11B 1/04 | (2006.01) | |
| C12N 1/12 | (2006.01) | |
| C11B 1/10 | (2006.01) | |

(52) U.S. Cl.
CPC ............ *C11B 1/04* (2013.01); *B02C 19/06* (2013.01); *B02C 19/065* (2013.01); *B02C 19/066* (2013.01); *C11B 1/02* (2013.01); *C11B 1/10* (2013.01); *C12N 1/066* (2013.01); *C12N 1/12* (2013.01); *C12P 7/64* (2013.01); *Y02E 50/13* (2013.01)

(58) Field of Classification Search
None
See application file for complete search history.

(56) References Cited

U.S. PATENT DOCUMENTS

| | | |
|---|---|---|
| 2010/0233761 A1 | 9/2010 | Czartoski et al. |
| 2011/0086386 A1 | 4/2011 | Czartoski et al. |
| 2012/0202255 A1 | 8/2012 | Suzuki |
| 2013/0302864 A1 | 11/2013 | Suzuki |
| 2015/0175954 A1 | 6/2015 | Kunita et al. |

FOREIGN PATENT DOCUMENTS

| | | |
|---|---|---|
| CN | 102504999 A | 6/2012 |
| JP | 2000-287671 A | 10/2000 |
| JP | 2012-520076 A | 9/2012 |
| WO | WO 2011/013707 A1 | 2/2011 |
| WO | WO 2012-099172 A1 | 7/2012 |
| WO | WO 2013/176261 A1 | 11/2013 |

OTHER PUBLICATIONS

Olmstead ("Low solvent, low temperature method for extracting biodiesel lipids from concentrated microalgal biomass", Bioresource Technology, 148 (2013), 615-619, Sep. 12, 2013) (Year: 2013).*
APEC Water ("pH Values of Water Completely explained" available at www.freedrinkingwater.com/water-education/quality-water-ph-page2.htm, published by APEC water, City of Industry, California, USA, webcapture from Jun. 22, 2019). (Year: 2019).*
The International Preliminary Report on Patentability and English translation of the Written Opinion of the International Searching Authority (Forms PCT/IB/338, PCT/IB/373 and PCT/ISA/237), dated Jun. 22, 2017, for International Application No. PCT/JP2015/006110.
Grimi et al., "Selective extraction from microalgae Nannochloropsis sp. using different methods of cell disruption", Bioresource Technology, vol. 153, 2014, pp. 254-259.
International Search Report (PCT/ISA/210) issued in PCT/JP2015/006110, dated Mar. 15, 2016.
Samarasinghe et al., "Algal cell rupture using high pressure homogenization as a prelude to oil extraction", Renewable Energy, vol. 48, 2012, pp. 300-308.
Spiden et al. "Quantitative evaluation of the ease of rupture of industrially promising microalgae by high pressure homogenization", Bioresource Technology, vol. 140, 2013, pp. 165-171.

\* cited by examiner

*Primary Examiner* — Robert J Yamasaki
*Assistant Examiner* — Charles Zoltan Constantine
(74) *Attorney, Agent, or Firm* — Birch, Stewart, Kolasch & Birch, LLP

(57) ABSTRACT

A method for algae disruption includes: a thermal treatment of microalgae belonging to Heterokontophyta at a pH of 3.5 or more and 9.5 or less and a temperature of 40° C. or more and 65° C. or less; and a physical treatment of the microalgae using a high pressure dispersion apparatus, the physical treatment following the thermal treatment.

15 Claims, 3 Drawing Sheets

METHOD FOR RUPTURE OF ALGAE

TECHNICAL FIELD

The present disclosure relates to a method for algae disruption, and a method for lipid extraction from algae using the same.

BACKGROUND ART

Environmental concerns such as global warming have been a focus of interest and attention in recent years. Under these circumstances, various studies have been conducted on reduction of $CO_2$ emission, and reduction of $CO_2$ concentration in the air by $CO_2$ fixation. For example, active attempts have been made to use biomass, a carbon neutral material, as an energy source alternative to fossil fuels.

Algae are known to produce lipid. If extracted efficiently, the lipid produced by the algae would be an energy source alternative to the fossil fuels. The lipid would also be used as materials for various products. However, cell walls of the algae constitute a major obstacle to the lipid extraction from the algae. The cell walls of the algae are generally hard and flexible, and cannot be disrupted easily. Thus, efficient recovery of the products such as lipid from the algae has been difficult.

For example, Patent Document 1 describes a method of recovering oil-based compounds such as lipid from biomass. According to this method, a biomass suspension with adjusted pH is brought into contact with a nonpolar solvent so that cell products are recovered from the nonpolar solvent and a polar biomass solution.

CITATION LIST

Patent Document

[Patent Document 1] Japanese Unexamined Patent Publication (Japanese Translation of PCT Application) No. 2012-520076

SUMMARY OF THE INVENTION

Technical Problem

However, the method according to Patent Document 1 cannot achieve a sufficient yield of lipid. Further, Patent Document 1 describes that conditions, a pH of 1 and a treatment temperature of 120° C. or more, are required for the high yield of lipid. Thus, special equipment resistant to high temperature and strong acid is required, which makes commercialization of the method very difficult.

If the algae were efficiently disrupted, improved yield of lipid from the algae would be expected.

In view of the foregoing, it is therefore an object of the present disclosure to efficiently disrupt microalgae belonging to Heterokontophyta.

Solution to the Problem

According to an aspect of a method for algae disruption, the method includes: a thermal treatment of microalgae belonging to Heterokontophyta at a pH of 3.5 or more and 9.5 or less and a temperature of 40° C. or more and 65° C. or less, and a physical treatment of the microalgae using a high pressure dispersion apparatus, the physical treatment following the thermal treatment.

Advantages of the Invention

The method for algae disruption according to the present disclosure allows for efficient disruption of microalgae belonging to Heterokontophyta.

DESCRIPTION OF EMBODIMENTS

<Microalgae Belonging to Heterokontophyta>

Figure 1:
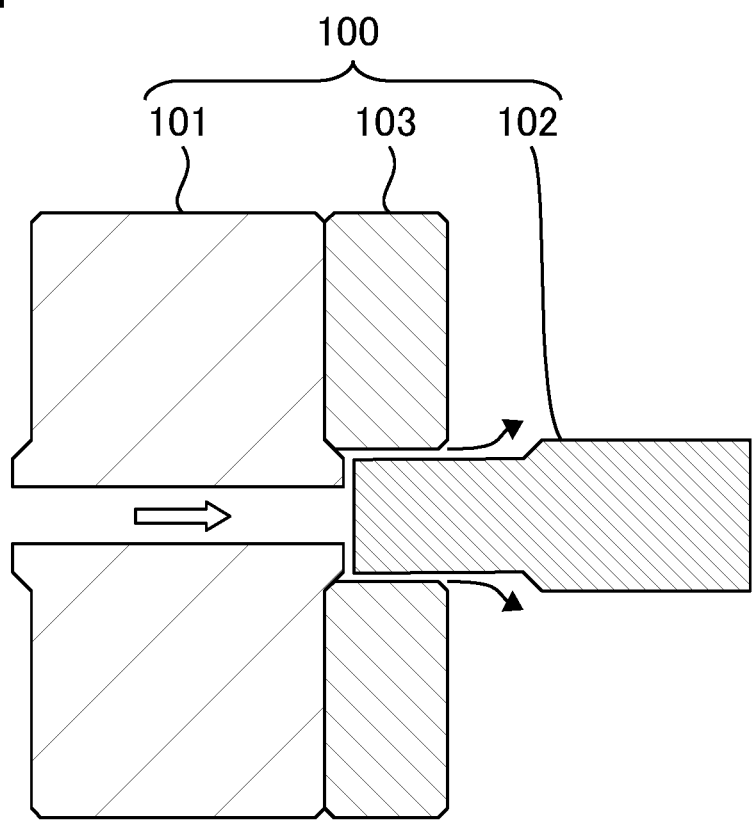
FIG. 1 A cross-sectional view illustrating an example of a homogenizing valve of a high pressure dispersion apparatus.

According to the present disclosure, microalgae belonging to Heterokontophyta are microalgae belonging to the Division Heterokontophyta. The microalgae designate organisms which produce oxygen through photosynthesis except for Bryophyta, Pteridophyta, and Spermatophyta and have a cell size of 1-100 μm in diameter. The cell size is a longitudinal diameter of a cell measured with an optical microscope at 400-fold magnification. Examples of the microalgae belonging to Heterokontophyta may include microalgae of the classes Bacillariophyceae and Eustigmatophyceae. Examples of the microalgae of the class Bacillariophyceae may include microalgae of the genera *Chaetoceros*, *Nitzschia*, and *Skeletonema*. Examples of the microalgae of the class Eustigmatophyceae may include microalgae of the genus *Nannochloropsis*. Among these microalgae, the microalgae of the class Eustigmatophyceae are suitable, and of the genus *Nannochloropsis* are more suitable in view of lipid productivity and lipid recovery. Examples of the algae of the genus *Nannochloropsis* may include *Nannochloropsis oculata*, *Nannochloropsis sauna*, and *Nannochloropsis gaditana*. The microalgae may be harvested from natural fields such as meres and ponds, cultivated, or obtained commercially.

<Disruption Method>

A method for algae disruption according to the present embodiment includes, a thermal treatment of the microalgae belonging to Heterokontophyta at a hydrogen ion concentration (pH) in a predetermined range and a temperature in a predetermined range, and a physical treatment of the microalgae using a high pressure dispersion apparatus, the physical treatment following the thermal treatment.

According to the disruption method of the present embodiment, algae harvested or cultivated, and dispersed in a dispersion medium may be disrupted as they are. A treatment solution containing microalgae may be diluted or concentrated to adjust the concentration of the microalgae in the solution (hereinafter may be referred to as an "algal concentration") before the disruption. Alternatively, a dispersion medium may be substituted or an additive may be added. The algae may be preserved at low or normal temperature, or cryopreserved. It is beneficial that the microalgae have not been exposed to a temperature of 80° C. or more before the disruption.

The algal concentration is not particularly limited. In view of improved productivity, easy disruption of algae, and recovery of lipid, the algal concentration is suitably 0.5 g/L or more, more suitably 0.8 g/L or more, much more suitably 5 g/L or more, even more suitably 10 g/L or more. Further, in view of easy disruption of algae, recovery of lipid, and flowability of the treatment solution, the algal concentration is suitably 200 g/L or less, more suitably 100 g/L or less, much more suitably 50 g/L or less, even more suitably 30 g/L or less, far more suitably 20 g/L or less.

How to adjust the algal concentration is not particularly limited. To increase the concentration, for example, filtration, compression, centrifugation, gravity settling, flocculation sedimentation, floatation, or evaporation of a dispersion medium may be performed. For example, a flocculant such as aluminum sulfate is added for flocculation sedimentation of the algae, and part of the supernatant is disposed to increase the concentration. Alternatively, after the flocculation sedimentation of the algae, the algae sediment may be collected and resuspended for condensation. Two or more methods may be combined for multistage condensation. A thermal treatment and a physical treatment may be performed at different concentrations. To dilute the solution, water or any other liquid may be added to the solution. Note that the concentration of the microalgae in the treatment solution is measured by a method described in Examples.

A dispersion medium used in the treatment solution is not particularly limited as long as the treatment solution has a pH within a predetermined range. Water is suitably used in view of cost efficiency. The water may be purified, or contain impurities. The water may be seawater. The treatment solution may contain any one or more of additives including salt such as sodium chloride, a compound containing nitrogen or phosphorus, trace metal, an inorganic flocculant, an organic flocculant, a chelating agent, and a buffer. If the microalgae are cultivated in a culture medium containing water as a main ingredient, the culture medium with the cultivated microalgae may be subjected to a thermal treatment directly, or after dilution or any other suitable process. If the culture medium or a dilution thereof is used as the treatment solution, the treatment solution may contain various components generally contained in a common culture medium. For dilution of the culture medium, water or an aqueous solution containing a predetermined additive may be used. The culture medium may be substituted with water or an aqueous solution containing a predetermined additive before the disruption.

—Thermal Treatment— pH

In view of efficient disruption of the microalgae, the thermal treatment is performed at a pH of 3.5 or more, suitably 3.8 or more, more suitably 4.0 or more, much more suitably 4.5 or more, even more suitably 5.0 or more. Further, in view of efficient disruption of the microalgae, the pH is 9.5 or less, suitably 9.0 or less, more suitably 8.5 or less, much more suitably 8.0 or less, even more suitably 7.5 or less, still more suitably 7.0 or less, far more suitably 6.5 or less, a lot more suitably 6.0 or less.

The pH may be measured in a treatment solution at 25° C. by a method in conformity with JIS Z8802.

Treatment Temperature

In view of efficient disruption of the microalgae, the thermal treatment is performed at a temperature of 40° C. or more, suitably 42° C. or more, more suitably 43° C. or more, much more suitably 45° C. or more. Further, in view of efficient disruption of the microalgae, the temperature is 65° C. or less, suitably 62° C. or less, more suitably 60° C. or less, much more suitably 57° C. or less, even more suitably 55° C. or less, still more suitably 52° C. or less, far more suitably 50° C. or less.

Treatment Time

The thermal treatment time is a period during which the temperature of the treatment solution is maintained within the above-described temperature range. In view of efficient disruption of the microalgae, the treatment time is suitably 0.5 hours or more, more suitably 1 hour or more, much more suitably 3 hours or more, even more suitably 5 hours or more, still more suitably 8 hours or more, far more suitably 10 hours or more, yet more suitably 20 hours or more, a lot more suitably 24 hours or more, a great deal more suitably 48 hours or more. In view of production efficiency, the upper limit of the treatment time may suitably be 96 hours or less, more suitably 72 hours or less.

The thermal treatment may be continuously performed for a predetermined time, or performed in several steps such that the sum of the treatment times of these steps is the predetermined time.

The pH, the temperature, and the time respectively within the above-described ranges may be combined as appropriate. In particular, in view of efficient disruption of the microalgae, the pH is suitably 5.0 or more and 7.5 or less, the temperature is suitably 45° C. or more and 60° C. or less, and the treatment time is suitably 10 hours or more.

The thermal treatment may be performed in an open or closed treatment tank. The temperature in the treatment tank may be controlled by a generally known method. For example, a heat source, and a controller which turns the heat source on/off to control the temperature in the tank to a predetermined level may be provided. The temperature may be controlled at a general industrial precision level, for example, within a tolerance of ±5° C. or less, suitably ±3° C. or less, more suitably ±1° C. or less. If the temperature cannot be controlled easily, it is sufficient for the sum of the periods during which the temperature of the treatment solution is in a predetermined temperature range to be the predetermined time. The heat source may be arranged inside or outside the treatment tank. The treatment tank may be a batch type tank or a flow type tank. If the flow type tank is used, the tank may have the shape of a passage through which the treatment solution flows. The thermal treatment may be performed at normal pressure, or in a pressurized or depressurized environment.

The treatment temperature may be measured with, for example, a thermometer or temperature sensor inserted in the treatment solution. Alternatively, a noncontact temperature sensor may be used to measure the temperature of the treatment solution. An ambient or external temperature of the treatment tank may be measured instead of directly measuring the temperature of the treatment solution. In such a case, a correlation coefficient between the ambient or external temperature and the temperature of the treatment solution is obtained in advance, and the ambient or external temperature may be converted into the temperature of the treatment solution. Alternatively, the output of the thermometer or temperature sensor may be sent to a recorder to record the temperature continuously or periodically such that the thermal treatment time is controlled with high precision.

If the pH of the treatment solution is different from the predetermined value, acid or alkali may be added to the treatment solution to adjust the pH. Any kinds of acid may be used without particular limitation, and organic acids, mineral acids, or a mixture of these acids may be used. For example, acetic acid, citric acid, phosphoric acid, hydrochloric acid, nitric acid, or sulfuric acid may be used. Any kinds of alkali may be used without particular limitation, and sodium carbonate, ammonia, or sodium hydroxide may be used. A buffer solution may be used as a dispersion medium. The buffer solution may be selected depending on the pH required. For example, a buffer solution containing acetic acid, citric acid, phosphoric acid, sodium carbonate, or any other suitable component may be used.

During the thermal treatment, any additive may be added to the treatment solution. However, it is not necessary to actively add enzymes having the action of decomposing cell walls, such as hemicellulase, cellulase, pectinase, and laminarinaze. Further, it is not necessary to actively add agents having the action of decomposing cell walls, such as salt, alkali, a surfactant, and a detergent. Note that these enzymes or agents may be contained in the treatment solution.

—Physical Treatment—

The physical treatment may be performed using a high pressure dispersion apparatus. The high pressure dispersion apparatus is basically an apparatus which allows a treatment solution containing a dispersoid such as solid or droplet particles to pass through a narrow channel in a pressurized state, and then rapidly depressurizes the treatment solution to further disperse or pulverize the dispersoid such as the solid or droplet particles. The high pressure dispersion apparatus is also suitable from the viewpoint of bulk handling in an industrial scale.

A high pressure pump may be used to pressurize the treatment solution. The channel having a narrow space through which the treatment solution passes may have any structure as long as a predetermined pressure is applied to the treatment solution. The width of the narrow space may suitably be changed depending on the pressure required or any other conditions. For example, the channel may be a straight pipe having a diameter of 1 μm to 2000 μm. Alternatively, the channel may have an orifice having a diameter of 1 μm to 2000 μm in the halfway of the straight pipe. A slit having a width of 1 μm to 2000 μm may be formed in the halfway of the straight pipe. Further, a channel may be formed in a gap between a tip end of a valve and a valve rest, and the opening of the valve is adjusted to control the width of the gap in a range from 1 μm to 2000 μm. Channels each having a size of 1 μm to 2000 μm may be arranged to face each other to allow the treatment solutions respectively flowing through the channels to collide with each other. Moreover, the flow direction of a channel may be changed abruptly by bending the channel at a right angle so that the treatment solution collides against the wall of the channel.

Apparatuses of various different configurations may be used as the apparatus for performing the above-described treatment. In view of efficient disruption of the microalgae, for example, a homogenizing valve-type high pressure dispersion apparatus having a homogenizing valve, and a chamber-type high pressure dispersion apparatus having a chamber are suitably used. In particular, the chamber-type high pressure dispersion apparatus is suitably used from the viewpoint of low-volume handling, and the homogenizing valve-type high pressure dispersion apparatus is suitably used in view of bulk handling in an industrial scale. FIG. 1 shows an example of a homogenizing valve 100. The homogenizing valve 100 includes a homogenizing valve seat (valve rest) 101 through which a discharge port is formed, a homogenizing valve body 102 facing the discharge port of the homogenizing valve seat 101, and an impact ring 103 surrounding the homogenizing valve body 102. When passing through a gap formed by the homogenizing valve seat 101, the homogenizing valve body 102, and the impact ring 103, the treatment solution is greatly pressurized, and then rapidly depressurized after having passed through the gap. The dispersoid in the treatment solution discharged through the discharge port collides against the homogenizing valve body 102 and the impact ring 103. Then, the dispersoid is pulverized by a shear stress applied while the treatment solution passes through the gap, an impact force applied upon collision, and cavitation caused by pressure drop after the treatment solution has passed through the gap.

The shear stress applied to the dispersoid may be adjusted by changing the size of the gap formed by the homogenizing valve seat 101, the homogenizing valve body 102, and the impact ring 103. The surface of the homogenizing valve seat 101 and the surface of the homogenizing valve body 102 facing each other may be made flat and smooth. To lengthen the channel and apply a sufficiently high shear stress to the dispersoid, the channel may be provided with recesses and protrusions on a wall forming the channel. The impact ring 103 may be omitted.

For the physical treatment, the chamber-type high pressure dispersion apparatus may also be used. The chamber-type high pressure dispersion apparatus includes an apparatus in which the flows of the treatment solution collide with each other, an apparatus in which the treatment solution collides against a wall surface, and an apparatus in which such collision does not occur.

Figure 2:
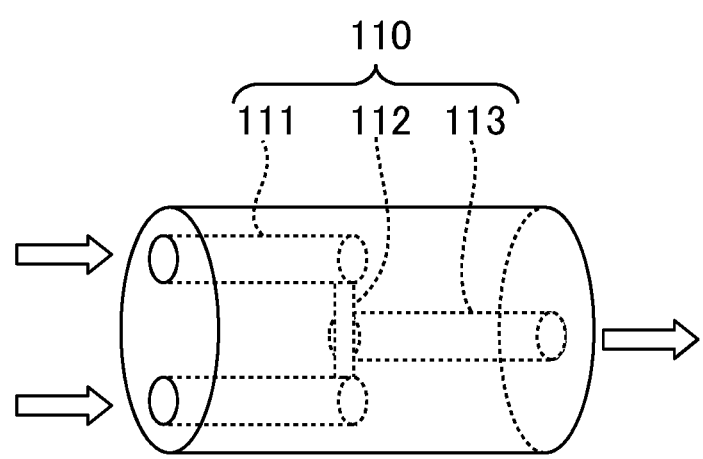
FIG. 2 A perspective view illustrating an example of a chamber of a high pressure dispersion apparatus.

The chamber-type high pressure dispersion apparatus which allows the flows of the treatment solution to collide with each other includes a chamber 110 as shown in FIG. 2, for example. The chamber 110 includes a plurality of inflow ducts 111 into which the treatment solution flows, shear ducts 112 as many as the inflow ducts 111, and a single outflow duct 113, which are sequentially coupled. The ends of the respective shear ducts 112 adjacent to the outflow duct 113 are connected together, and the flows of the treatment solution collide with each other at the connected ends. The dispersoid is pulverized by a shear stress applied in the shear ducts 112 narrower than the inflow ducts 111 and the outflow duct 113, an impact force applied upon collision of the flows of the treatment solution, and cavitation caused by pressure drop in the outflow duct 113.

Figure 3:
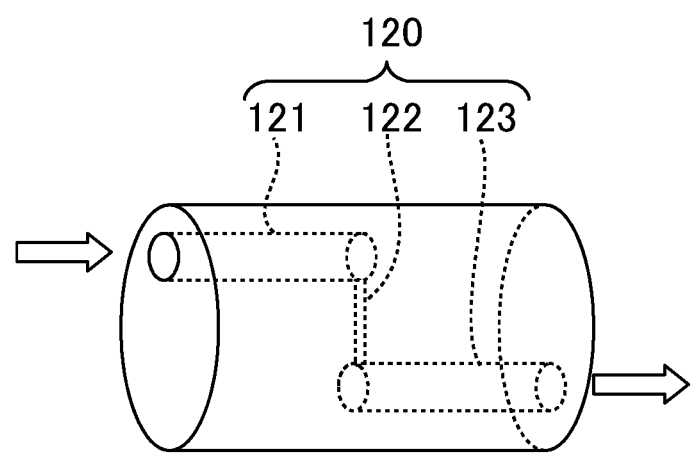
FIG. 3 A perspective view illustrating an example of a chamber of a high pressure dispersion apparatus.

The chamber-type high pressure dispersion apparatus which allows the treatment solution to collide against the wall surface includes a chamber 120 as shown in FIG. 3, for example. The chamber 120 includes a single liquid inflow duct 121, a single shear duct 122, and a single outflow duct 123, which are sequentially coupled. The shear duct 122 and the outflow duct 123 form a right angle so that a liquid flow passing through the shear duct 122 collides against the inner wall of the outflow duct 123. The dispersoid is pulverized by a hear stress applied in the shear ducts 122, an impact force applied upon collision of the treatment solution against the wall surface, and cavitation caused by pressure drop in the outflow duct 123.

The chamber-type high pressure dispersion apparatus which does not allow the collision of the treatment solution to occur includes, for example, a narrow shear duct in a channel. The dispersoid is pulverized by a shear stress applied in the shear duct and cavitation caused by pressure drop in an outflow duct wider than the shear duct.

The high pressure dispersion apparatus is not limited to those described above, and other high pressure dispersion apparatuses may also be used.

Irrespective of the type, when the high pressure dispersion apparatus is used for the physical treatment of the microalgae, a pressure (inlet pressure) applied to the treatment solution is 10 MPa or more in terms of gauge pressure, suitably 30 MPa or more, more suitably 50 MPa or more, much more suitably 80 MPa or more, in view of efficient disruption of the algae. In view of cost efficiency, the pressure is suitably 200 MPa or less, more suitably 150 MPa or less, much more suitably 120 MPa or less. Further, in view of efficient disruption of the algae and cost efficiency, the pressure after depressurization (outlet pressure) may be an atmospheric pressure (an absolute pressure of 0.1 MPa). There is no need to reduce the outlet pressure exactly to the atmospheric pressure depending on the structure of the channel or any other conditions. The outlet pressure is suitably 0.3 MPa or less (in terms of absolute pressure), more suitably 0.2 MPa or less, much more suitably 0.15 MPa or less, even more suitably 0.11 MPa or less.

Examples of the homogenizing valve-type high pressure dispersion apparatus include a pressure homogenizer (SMT Co., Ltd), a high pressure homogenizer (IZUMI FOOD MACHINERY Co., Ltd.), and a Mini-Lab 8.3 H (Rannie). Examples of the chamber-type high pressure dispersion apparatus include a microfluidizer (Microfluidics), Nanovator (SG Engineering Corporation, Yoshida Kikai Co., Ltd.), Star Burst (SUGINO MACHINE LIMITED), Ultimizer (SUGINO MACHINE LIMITED), Genus PY (Hakusui Tech Co., Ltd.), and DeBEE 2000 (BEE International). Among these apparatuses, Nanovator is suitably used from the viewpoint of low-volume handling, and the pressure homogenizer is suitably used from the viewpoint of bulk handling in an industrial scale.

Performing the physical treatment after the thermal treatment allows the microalgae belonging to Heterokontophyta to be efficiently disrupted. For the disruption of the microalgae belonging to Heterokontophyta, the above-described combination of the thermal and physical treatments improves the disruption efficiency more significantly than in the case where the physical treatment is solely performed. In the method for algae disruption according to the present embodiment, the thermal treatment is performed at a temperature of about 40° C. to 65° C. At a temperature within this range, the thermal treatment consumes less energy even if it lasts for several hours to several tens of hours, which maintains the cost very low. Thus, as compared with the case where the physical treatment is solely performed, the disruption efficiency improves, and in addition, substantial efficiency in consideration of energy and cost required improves significantly. Even if the thermal treatment lasts for several tens of hours to several days, the energy required is still low within this temperature range, which contributes to cutting down of the cost of the thermal treatment. Further, the cycle time also falls within a tolerable range, which substantially improves the disruption efficiency to a sufficient degree.

The physical treatment may be repeated several times after the thermal treatment. The physical treatment may directly follow the thermal treatment without any other treatment performed between the thermal and physical treatments. The physical treatment may be performed immediately after the thermal treatment while, the physical treatment may be performed after the treatment solution is once preserved after the thermal treatment. For the preservation of the treatment solution, the preservation temperature is suitably a normal temperature of about 15 to 25° C. in view of reduction of energy required. Further, the preservation temperature is suitably as low as about 5 to 15° C. in view of reducing the risk of alteration of lipid. Alternatively, the treatment solution may be cryopreserved. After the thermal treatment and before the physical treatment, concentration or dilution of the treatment solution, substitution of the dispersion medium, or adjustment of the pH of the treatment solution may also be performed.

<Lipid Extraction Method>

The disruption method according to the present embodiment may also be used as a lipid extraction method in combination with a process of lipid recovery. The higher the disruption rate is, the higher the yield of lipid extracted from the treatment solution containing the microalgae becomes. Thus, if the microalgae belonging to Heterokontophyta are disrupted by the method of the present embodiment which allows efficient disruption of the algae, and lipid is extracted from the microalgae thus disrupted, the yield of the lipid significantly increases. Further, increasing the disruption rate during the disruption significantly reduces the amount of the solvent used for the extraction, as well as energy and/or cost required for the extraction.

—Lipid—

In the context of the present disclosure, the lipid may include simple lipid, complex lipid, and derived lipid. The simple lipid may include an ester of fatty acid and various types of alcohols, such as fats and oils or fatty acid ester. The complex lipid may include phospholipid containing fatty acid, alcohol and phosphoric acid, and glycolipid containing fatty acid, alcohol and sugar. The derived lipid may include water-insoluble fatty acid, higher alcohol, sterol, terpene, and fat-soluble vitamins, which are products of hydrolysis of the simple or complex lipid. In view of recovery of lipid, the simple or complex lipid is suitable, the simple lipid is more suitable, and fats and oils are much more suitable.

—Fats and Oils—

Fats and oils designate esters of fatty acid and glycerin, in particular, neutral lipid such as monoglyceride, diglyceride, and triglyceride. The fatty acid constituting the fats and oils is not limited, and may include various kinds of fatty acids.

—Fatty Acid—

Fatty acid may be any of short-chain fatty acids having a carbon number of 2-4, medium-chain fatty acids having a carbon number of 5-12, and long-chain fatty acids having a carbon number of 12 or more. The fatty acid may be saturated or unsaturated. Examples of the saturated fatty acid may include decanoic acid, dodecanoic acid, tetradecanoic acid, hexadecanoic acid, octadecanoic acid, and icosanoic acid. Examples of monounsaturated fatty acid may include 9-hexadecenoic acid and 9-octadecenoic acid. Examples of polyunsaturated fatty acid may include 9,12-octadecadienoic acid, 6,9,12-octadecatrienoic acid, 5,8,11,14-icosatetraenoic acid, 9,12,15-octadecatrienoic acid, 5,8,11,14,17-icosapentaenoic acid, and 4,7,10,13,16,19-docosahexaenoic acid.

—Fatty Acid Esters—

Fatty acid esters are esters of fatty acid and alcohol, except for fats and oils, and may include wax which is an ester of long-chain fatty acid and higher monohydric or dihydric alcohol, and a medium-chain fatty acid ester which is an ester of medium-chain fatty acid and lower or higher alcohol.

—Lipid Recovery Process—

A process of the lipid recovery is not particularly limited as long as the lipid is separated from a treatment solution containing disrupted microalgae. For example, the lipid recovery may be achieved by solvent extraction, centrifugation, standing, column chromatography, or any other suitable technique. One or a combination of two or more of these techniques may be adopted. Above all, in view of recovery of lipid, one or a combination of two or more of solvent extraction, centrifugation, and standing is suitable.

In particular, a combination of solvent extraction and centrifugation, or a combination of solvent extraction and standing is suitable.

For the solvent extraction, a solution for extraction may be added to, and mixed with, the treatment solution which has gone through the disruption of the microalgae. The mixture thus obtained may be stirred. Lipid eluted from the microalgae dissolves in the solvent. Thus, a solvent phase and an aqueous phase are separated to recover the solvent phase, thereby yielding the lipid.

A solvent used for the solvent extraction may be, for example: esters such as methyl acetate and ethyl acetate; chain and cyclic ethers such as tetrahydrofuran and diethyl ether; polyethers such as polyethylene glycol; halogenated hydrocarbons such as dichloromethane, chloroform, and carbon tetrachloride; hydrocarbons such as hexane, cyclohexane, and petroleum ether; aromatic hydrocarbons such as benzene and toluene; pyridines; alcohols such as butanol, pentanol, hexanol, and isopropyl alcohol (2-propanol); polyalcohols such as butylene glycol; ketones such as methyl ethyl ketone; and supercritical carbon dioxide. One or a combination of two or more of these substances may be used.

Among these solvents, nonpolar solvents are suitably used in view of recovery of lipid. Examples of the nonpolar solvents may include halogenated hydrocarbons, hydrocarbons, and aromatic hydrocarbons. In particular, the hydrocarbons are suitable, among which hexane is more suitable. Further, a solvent compatible to water, such as methanol, ethanol, propanol, ethylene glycol, propylene glycol, and acetone, may be supplementarily added to the nonpolar solvent. Moreover, supercritical extraction using supercritical carbon dioxide may also be adopted. In addition, immersion, decoction, leaching, reflux extraction, subcritical extraction, or any other technique may also be adopted. For example, a method described in "Biochemical Experimentation Method 24—Method of Experimenting Lipid Metabolism in Plants" (Akihiro YAMADA, Japan Scientific Societies Press, pp. 3-4) can also be referred to.

The solvent extraction may be performed at any temperature without particular limitation. However, in view of recovery of lipid, the temperature is suitably 10° C. or more, more suitably 20° C. or more. In view of recovery of lipid and cost of heating the solvent, the temperature is suitably 60° C. or less, more suitably 50° C. or less, much more suitably 40° C. or less.

The solvent extraction may be performed once, or twice or more. If the solvent extraction is performed twice or more, it may be performed with the same solvent or different solvents.

The centrifugation may be performed with a generally known apparatus such as a disk centrifuge, a cylindrical centrifuge, a decanter centrifuge, or any other type of centrifuge. In this case, a centrifugal force may suitably be 500 G or more, more suitably 1000 G or more, in view of recovery of lipid. Further, in view of cost efficiency, the centrifugal force may suitably be 10000 G or less, more suitably 5000 G or less, much more suitably 2000 G or less.

The centrifugation may suitably be performed for 1 minute or more, more suitably 5 minutes or more, much more suitably 10 minutes or more in view of recovery of lipid. Further, in view of cost efficiency, the centrifugation time may suitably be 80 minutes or less, more suitably 40 minutes or less, much more suitably 20 minutes or less.

The centrifugation may be performed at any temperature without particular limitation. However, in view of recovery of lipid and cost efficiency, the temperature may suitably be 10° C. or more, more suitably 15° C. or more, and suitably be 50° C. or less, more suitably 40° C. or less.

If the solvent extraction and the centrifugation are combined, a solvent phase and an aqueous phase can be separated quickly by the centrifugation.

During the standing process, the reaction solution is allowed to stand until lipid and an aqueous phase are separated. If the standing process and the solvent extraction are combined, the reaction solution may be allowed to stand until a solvent phase and an aqueous phase are separated.

According to the disclosed method for extracting the lipid from the algae, the lipid accumulated in the microalgae may be extracted with high yield by such a simple operation.

The lipid extracted from the microalgae may be used directly, or indirectly after purification or decomposition, as biofuels such as a biodiesel fuel. Further, the lipid may also be used as materials for functional food, pharmaceuticals, chemical products, and cosmetics.

The method of extracting and recovering lipid from the disrupted microalgae has been described. However, products other than the lipid, such as sugar and protein, may also be extracted and recovered for use. These products may be extracted and recovered by a generally known method.

Regarding the above-described embodiment, the present disclosure further discloses a method for disruption of the following algae and a method for extracting lipid from the algae.

<1>

A method for algae disruption, comprising:

a thermal treatment of microalgae belonging to Heterokontophyta at a pH of 3.5 or more, suitably 3.8 or more, more suitably 4.0 or more, much more suitably 4.5 or more, even more suitably 5.0 or more, and 9.5 or less, suitably 9.0 or less, more suitably 8.5 or less, much more suitably 8.0 or less, even more suitably 7.5 or less, still more suitably 7.0 or less, far more suitably 6.5 or less, a lot more suitably 6.0 or less, and a temperature of 40° C. or more, more suitably 42° C. or more, much more suitably 43° C. or more, even more suitably 45° C. or more, and 65° C. or less, suitably 62° C. or less, more suitably 60° C. or less, even more suitably 57° C. or less, still more suitably 55° C. or less, far more suitably 52° C. or less, a lot more suitably 50° C. or less; and a physical treatment of the microalgae belonging to Heterokontophyta using a high pressure dispersion apparatus, the physical treatment following the thermal treatment.

<2>

The method for algae disruption of <1>, wherein the microalgae are of the genus *Nannochloropsis*.

<3>

The method for algae disruption of <1> or <2>, wherein the thermal treatment is suitably performed for 0.5 hours or more, more suitably 1 hour or more, much more suitably 3 hours or more, even more suitably 5 hours or more, still more suitably 8 hours or more, far more suitably 10 hours or more, yet more suitably 20 hours or more, a lot more suitably 24 hours or more, a great deal more suitably 48 hours or more.

<4>

The method for algae disruption of any one of <1> to <3>, wherein the thermal treatment is suitably performed for 96 hours or less, more suitably 72 hours or less.

<5>

The method for algae disruption of any one of <1> to <4>, wherein the physical treatment is performed, using the high pressure dispersion apparatus, by applying a gauge pressure which is suitably 10 MPa or more, more suitably 30 MPa or more, much more suitably 50 MPa or more, even more suitably 80 MPa or more, and suitably 200 MPa or less, more suitably 150 MPa or less, even more suitably 120 MPa or less, and reducing the pressure to an absolute pressure which is suitably 0.3 MPa or less, more suitably 0.2 MPa or less, much more suitably 0.15 MPa or less, even more suitably 0.11 MPa or less, still more suitably an atmospheric pressure (0.1 MPa).

<6>

The method for algae disruption of any one of <1> to <5>, wherein the thermal treatment is performed without intentionally adding an enzyme which decomposes cell walls.

<7>

The method for algae disruption of any one of <1> to <6>, wherein the thermal treatment is performed at a pH of 5.0 or more and 7.5 or less and a temperature of 45° C. or more and 60° C. or less for 10 hours or more.

<8>

The method for algae disruption of any one of <1> to <7>, wherein the high pressure dispersion apparatus is a homogenizing valve-type high pressure dispersion apparatus or a chamber-type high pressure dispersion apparatus.

<9>

A method for extracting lipid from algae, the method comprising:
recovery of lipid from algae disrupted by the method for algae disruption of any one of <1> to <8>.

<10>

The method for extracting lipid of <9>, wherein the recovery of the lipid is performed by one or a combination of two or more of solvent extraction, centrifugation, standing, and column chromatography, suitably one or a combination of two or more of the solvent extraction, the centrifugation and the standing, more suitably a combination of the solvent extraction and the centrifugation, or a combination of the solvent extraction and the standing.

<11>

The method for extracting lipid of <10>, wherein the solvent used for the solvent extraction for the recovery of the lipid is suitably a nonpolar solvent, more suitably hydrocarbons, much more suitably hexane.

<12>

The method for extracting lipid of <10> or <11>, wherein the solvent extraction for the recovery of the lipid is suitably performed at a temperature of 10° C. or more, more suitably 20° C. or more, and suitably 60° C. or less, more suitably 50° C. or less, much more suitably 40° C. or less.

<13>

The method for extracting lipid of any one of <10> to <12>, wherein the centrifugation for the recovery of the lipid is suitably performed at a centrifugal force of 500 G or more, more suitably 1000 G or more, and suitably 10000 G or less, more suitably 5000 G or less, much more suitably 2000 G or less.

<14>

The method for extracting lipid of any one of <10> to <13>, wherein the centrifugation for the recovery of the lipid is suitably performed for 1 minute or more, more suitably 5 minutes or more, much more suitably 10 minutes or more, and suitably 80 minutes or less, more suitably 40 minutes or less, much more suitably 20 minutes or less.

<15>

The method for extracting lipid of any one of <10> to <13>, wherein the centrifugation for the recovery of the lipid is suitably performed at a temperature of 10° C. or more, more suitably 15° C. or more, and suitably 50° C. or less, more suitably 40° C. or less.

EXAMPLES

The present disclosure will be described in further detail by way of examples. Examples described below are merely exemplary ones, and do not limit the present invention.

<Algae Body Used>

A seawater sample containing algae bodies was collected from a coastal region of Ishigaki Island, Okinawa. The seawater sample thus collected was concentrated with a filter, and a single algal strain was isolated with a micropipette. The algae body thus isolated was cultivated in a culture solution (Daigo's IMK medium, Wako Pure Chemical Industries, Ltd.), and the algae body was proliferated using a culture solution (f/2 medium). As a result of analysis of part of the algae body by University of Texas (UTEX Culture Collection), this algae body was identified as *Nannochloropsis sauna*.

Further, *Nannochloropsis oculata* "Yanmarine K-1" (Chlorella Industry Co., Ltd., liquid constituting the treatment solution: seawater, algal concentration: 50 g/L) was obtained, and used for experiments.

<Counting Cells>

Two μL of a diluted treatment solution was injected into a counting chamber of a bacteria counter (Sunlead Glass Corp.), and observed with an optical microscope (ECLIPSE80i of Nikon) at 400-fold magnification to count cells in blocks. In the counting chamber of the bacteria counter, the blocks each having a size of 0.05 mm square were used. The counting chamber included 25 counting areas (5×5) each having 16 blocks (4×4), 0.05 mm square each. Cells were counted in five of the counting areas located on a diagonal line extending from the upper right corner to the lower left corner in a field of view of the microscope. More specifically, cells were counted in 80 blocks, 0.05 mm square each (five sets of 16 blocks). The depth of the counting chamber of the bacteria counter was 0.020 mm, and a volume per block of 0.05 mm square was $\frac{1}{20000}$ mm$^3$. The total number of cells counted was divided by the total volume of the corresponding blocks ($\frac{1}{20000}$ mm$^3$×80 blocks), and the obtained value was multiplied by the dilution rate of the dilution used for the counting to obtain the cell count per ml of the sample before dilution. The diluent used was Daigo's artificial seawater SP (Wako Pure Chemical Industries, Ltd.).

<Calculation of Cell Disruption Rate>

The number of cells in the treatment solution was counted by the above-described cell counting method. The number of cells counted after the disruption was subtracted from the number of cells counted before the disruption, and the obtained value was divided by the number of cells counted before the disruption, and then multiplied by 100. Thus, the cell disruption rate (%) was obtained.

<Measurement of Algal Concentration>

A treatment solution containing microalgae was placed in a centrifuge (CR22GIII, HITACHI, rotor: 18A) for centrifugation (15000 rpm, 5 minutes, 25° C.). After the supernatant was disposed, the product thus obtained was dispersed again in a 0.125 M citric acid-disodium hydrogen phosphate buffer (pH 5). The dispersion was vacuum-filtrated with a filter (Supor-450, Pall Corporation, pore size: 0.45 μm), and washed with an equal amount of distilled water. The filter that had trapped the algal bodies was moved into an aluminum cup, and dried at 105° C. for 2 hours. The weight of the dried filter was measured, and the tare of the filter was subtracted from the measured weight to obtain the algal concentration (g/L). If the treatment solution was not easily vacuum-filtered with the filter, the treatment solution was diluted to a suitable concentration, the weight of the dried filter was measured, the tare of the filter was subtracted from the measured weight, and then the obtained value was multiplied by the dilution ratio to obtain the algal concentration (g/L). Note that a 0.125 M citric acid-disodium hydrogen phosphate buffer (pH 5) may be used as a diluent.

<Thermal Treatment>

A treatment solution containing microalgae in a predetermined concentration was placed in a polyethylene vessel, and left stand in a chamber of a vacuum drier (ADP300, Yamato Scientific Co., Ltd.) preset at a predetermined temperature. The pressure in the chamber was set to an atmospheric pressure. After the lapse of a predetermined time, the sample was removed from the drier, and cooled at room temperature. If the sample was treated at 25° C. for comparison, the temperature in the laboratory was set to 25° C., and the sample was left stand in the laboratory. Further, if the sample was treated at 4° C. for comparison, the sample was left stand in a refrigerator (MPR-1411, Sanyo Electric Co., Ltd.). After the lapse of a predetermined time, the sample was removed from the refrigerator, and left stand until the temperature of the sample returned to room temperature.

<Physical Treatment>

The physical treatment was performed with a high pressure dispersion apparatus. As the high pressure dispersion apparatus, Nanovator "NM2-L200-D" (Yoshida Kikai Co., Ltd., cross-type nozzle, NVGL-XT160) or a pressure homogenizer "LAB2000" (SMT Corporation) was used. When Nanovator was used, the inlet pressure was 100 MPa in terms of gauge pressure, and the outlet pressure was 0.1 Mpa (atmospheric pressure) in terms of absolute pressure. First six fractions were excluded, and the seventh and subsequent fractions were collected. The number of passes was one. When the pressure homogenizer was used, the inlet pressure was 100 MPa in terms of gauge pressure, and the outlet pressure was 0.1 Mpa (atmospheric pressure) in terms of absolute pressure. First 300 cc of the treatment solution discharged after the start of the treatment was disposed, and the solution discharged thereafter was collected as the treatment sample. The number of passes was one.

<Measurement of Lipid Content in Dried Algal Body>

The lipid content in the algal body was analyzed by a method for lipid extraction from biological materials reported by E. G. Bligh and W. J. Dyer in 1959 (Bligh & Dyer Method) (E. G. Bligh, W. J. Dyer, Canadian journal of biochemistry and physiology, 37 (1959), pp. 911-917).

To 0.5 mL of an untreated sample, 100 µL of 1 mg/mL 7-pentadecanone (a methanol solution) was added as an internal standard. Then, 10 µL of 2 N HCl was added, and 500 µL of chloroform and 0.9 mL of methanol were added. After being stirred, the obtained solution was left stand at 25° C. for 30 minutes, and 500 µL of chloroform and 500 µL of 1.5% KCl were added. After being stirred, the obtained solution was centrifuged (centrifugal force: 1500 G, number of revolutions: 3000 r/min, temperature: 25° C., time: 15 minutes) with a centrifuge "himac CF7D2" (Hitachi Koki Co., Ltd.). Then, a lower chloroform phase was collected, and dried and solidified with nitrogen. Subsequently, 0.7 mL of a 0.5 N KOH-methanol solution (2.8 g of potassium hydroxide, 100 mL of methanol) was added, incubated at 80° C. for 30 minutes for saponification. Further, 1 mL of a 14% boron trifluoride solution was added, and incubated at 80° C. for 10 minutes for methyl esterification. Then, 1 ml of a solvent and 1 ml of saturated brine were added, stirred, and left stand at 25° C. for 30 minutes to obtain a solvent phase. Hexane was used as the solvent. The solvent phase thus obtained was collected, and fatty acid ester was identified and quantified by gas chromatography (GC) under the following conditions. The identification of the fatty acid ester was performed by determining whether the retention time of the fatty acid ester was identical to that of a reference material to be described later. The amount of the fatty acid ester detected through the GC analysis was calculated relative to the internal standard, and the total amount was obtained as the lipid content in the dried algal body.

Note that the solvent extraction method using chloroform and methanol, which is effective for simply measuring the lipid content in the algal body, is not suitable for industrial applications in view of safety, recovery, and recycling of the solvents used.

—GC Analysis—

Apparatus: Agilent technology 7890A

Column: DB1-MS (product of J&W Scientific, 20 m×100 µm×0.1 µm)

Furnace Temperature: 150° C. (0.5 min hold)-[40° C./min]-220° C. (0 min hold)-[20° C./min]-320° C. (2 min hold)-post run 2 min Carrier Gas: Hydrogen Makeup Gas: Helium Amount of Sample Injection: 5 µL Injection Mode: Split (Sprit Rate=75:1)

Injection Port Temperature: 300° C.

Detector: FID

Flow Rate in Column: 0.28 mL/min, Constant

Pressure (Gauge Pressure): 62.403 psi

Reference Material: the following fatty acid esters available from SIGMA: methyl laurate (C12), methyl myristate (C14), methyl palmitate (C16), methyl stearate (C18), methyl palmitoleate (C16:1), methyl oleate (C18:1), methyl linoleate (C18:2), methyl linolenate (C18:3), methyl eicosapentaenoate (C20:5), methyl docosahexaenoate (C22:6)

<Measurement of Lipid Yield>

Lipid was recovered by the solvent extraction described below. The lipid thus recovered was methyl-esterified, and the lipid content was quantified by the above-described GC analysis.

—Hexane Extraction—

To 0.5 mL of the treated sample, 1 mL of hexane was added. Then, the obtained product was stirred at 25° C. for 3 minutes, and centrifuged (centrifugal force: 1500 G, number of revolutions: 3000 r/min, temperature: 25° C., time: 15 minutes) with a centrifuge "himac CF7D2" (Hitachi Koki Co., Ltd.). Then, 400 µL of an upper hexane phase was collected, 40 µL of 1 mg/mL 7-pentadecanone (methanol solution) was added as an internal standard, and dried and solidified with nitrogen. Then, 0.7 mL of a 0.5N KOH-methanol solution (2.8 g of potassium hydroxide, 100 mL of methanol) was added, and incubated at 80° C. for 30 minutes for saponification. Further, 1 mL of a 14% boron trifluoride solution was added, and incubated at 80° C. for 10 minutes for methyl esterification. Then, 1 mL of a solvent and 1 mL of saturated brine were added, stirred, and then left stand at 25° C. for 30 minutes to obtain a solvent phase. Hexane was used as the solvent. The solvent phase thus obtained was collected, and fatty acid ester was identified and quantified by gas chromatography (GC) under the above-described conditions. The amount of the fatty acid ester detected through the GC analysis was calculated relative to the internal standard, and the total amount was obtained as the lipid content in hexane.

—Calculation of Lipid Yield—

The lipid yield using a hexane solvent was calculated by the following equation (1).

$$\text{Lipid yield (\%)} = \text{lipid content in hexane/lipid content in dried algal body} \times 100 \quad (1)$$

Example 1

As the microalgae belonging to Heterokontophyta, *Nannochloropsis* sauna (liquid comprising the treatment solution: artificial seawater (Daigo's artificial seawater SP, Nihon Pharmaceutical Co., Ltd., algal concentration: 1.0 g/L)) was used. The treatment solution had a pH of 7.3 at 25° C. To adjust the pH of the treatment solution to 5.0, 1 M HCl was dropped. The solution with the pH thus adjusted was subjected to a thermal treatment. The treatment was performed at 50° C. for an hour. After the thermal treatment, a physical treatment was performed with Nanovator at an inlet pressure of 100 MPa. The cell disruption rate was 38.6%.

Example 2

The disruption process was performed in the same manner as Example 1 except that the thermal treatment was performed for 2 hours. The cell disruption rate was 33.9%.

Example 3

The disruption process was performed in the same manner as Example 1 except that the thermal treatment was performed for 3 hours. The cell disruption rate was 45.8%.

Example 4

The disruption process was performed in the same manner as Example 1 except that the thermal treatment was performed for 5 hours. The cell disruption rate was 47.4%.

Example 5

The disruption process was performed in the same manner as Example 1 except that the thermal treatment was performed for 10 hours. The cell disruption rate was 60.5%.

Example 6

The disruption process was performed in the same manner as Example 1 except that the thermal treatment was performed for 24 hours. The cell disruption rate was 87.0%. The lipid yield after the disruption was 69%.

Example 7

The disruption process was performed in the same manner as Example 6 except that the physical treatment was performed at an inlet pressure of 50 MPa. The cell disruption rate was 75.9%. The lipid yield after the disruption was 70%.

Comparative Example 1

The disruption process was performed in the same manner as Example 1 except that neither the pH adjustment nor the thermal treatment was performed. Specifically, a treatment solution of *Nannochloropsis* sauna (liquid comprising the treatment solution: artificial seawater (Daigo's artificial seawater SP, Nihon Pharmaceutical Co., Ltd., algal concentration: 1.0 g/L)) was obtained, and then subjected to a physical treatment using Nanovator (a high pressure dispersion apparatus) at an inlet pressure of 100 MPa within 30 minutes after the sample was obtained. The pH was maintained at 7.3 and no thermal treatment was performed. The cell disruption rate was 16.9%.

Comparative Example 2

The disruption process was performed in the same manner as Example 1 except that no thermal treatment was performed. Specifically, a treatment solution of *Nannochloropsis* sauna (liquid comprising the treatment solution: artificial seawater (Daigo's artificial seawater SP, Nihon Pharmaceutical Co., Ltd., algal concentration: 1.0 g/L)), the pH of which was adjusted to 5.0 at 25° C. with 1 M HCl, was subjected to a physical treatment using Nanovator (a high pressure dispersion apparatus) at an inlet pressure of 100 MPa within 30 minutes after the sample was obtained. No thermal treatment was performed. The cell disruption rate was 18.7%. The lipid yield after the disruption was 6%.

Comparative Example 3

The disruption process was performed in the same manner as Example 1 except that the thermal treatment was performed at 25° C. The cell disruption rate was 16.1%.

Comparative Example 4

The disruption process was performed in the same manner as Example 1 except that the thermal treatment was performed at 25° C. for 2 hours. The cell disruption rate was 11.9%.

Comparative Example 5

The disruption process was performed in the same manner as Example 1 except that the thermal treatment was performed at 25° C. for 3 hours. The cell disruption rate was 13.2%.

Comparative Example 6

The disruption process was performed in the same manner as Example 1 except that the thermal treatment was performed at 25° C. for 10 hours. The cell disruption rate was 18.5%.

Comparative Example 7

The disruption process was performed in the same manner as Example 1 except that the thermal treatment was performed at 25° C. for 24 hours. The cell disruption rate was 16.1%.

Comparative Example 8

The disruption process was performed in the same manner as Example 1 except that the thermal treatment was performed at 80° C. The cell disruption rate was 21.8%.

Comparative Example 9

The disruption process was performed in the same manner as Example 1 except that the thermal treatment was performed at 80° C. for 2 hours. The cell disruption rate was 18.5%.

Comparative Example 10

The disruption process was performed in the same manner as Example 1 except that the thermal treatment was performed at 80° C. for 3 hours. The cell disruption rate was 24.8%.

Comparative Example 11

The disruption process was performed in the same manner as Example 1 except that the thermal treatment was performed at 80° C. for 10 hours. The cell disruption rate was 18.5%.

Comparative Example 12

The disruption process was performed in the same manner as Example 1 except that the thermal treatment was performed at 80° C. for 24 hours. The cell disruption rate was 23.0%.

Comparative Example 13

The disruption process was performed in the same manner as Comparative Example 2, and then an additional thermal treatment was performed at 50° C. for 24 hours. The cell disruption rate was 19.3%.

Example 8

The disruption process was performed in the same manner as Example 1 except that the thermal treatment was performed at 40° C. for 24 hours. The cell disruption rate was 49.5%. The lipid yield after the disruption was 33%.

Example 9

The disruption process was performed in the same manner as Example 1 except that the thermal treatment was performed at 45° C. for 24 hours. The cell disruption rate was 92.0%. The lipid yield after the disruption was 74%.

Example 10

The disruption process was performed in the same manner as Example 1 except that the thermal treatment was performed at 55° C. for 24 hours. The cell disruption rate was 81.2%. The lipid yield after the disruption was 73%.

Example 11

The disruption process was performed in the same manner as Example 1 except that the thermal treatment was performed at 60° C. for 24 hours. The cell disruption rate was 72.1%. The lipid yield after the disruption was 55%.

Comparative Example 14

The disruption process was performed in the same manner as Example 1 except that the thermal treatment was performed at 4° C. for 24 hours. The cell disruption rate was 19.9%.

Comparative Example 15

The disruption process was performed in the same manner as Example 1 except that the thermal treatment was performed at 37° C. for 24 hours. The cell disruption rate was 19.0%.

Comparative Example 16

The disruption process was performed in the same manner as Example 1 except that the thermal treatment was performed at 70° C. for 24 hours. The cell disruption rate was 29.4%.

Comparative Example 17

The disruption process was performed in the same manner as Example 1 except that the thermal treatment was performed at 80° C. for 24 hours. The cell disruption rate was 23.0%.

Table 1 shows the conditions and cell disruption rates of Examples 1-7, and Table 2 shows the conditions and cell disruption rates of Comparative Examples 1-13. Table 3 collectively shows the conditions and cell disruption rates of Examples 8-11 and Comparative Examples 14-17.

TABLE 1

|  | Example 1 | Example 2 | Example 3 | Example 4 | Example 5 | Example 6 | Example 7 |
|---|---|---|---|---|---|---|---|
| Algal body | N. salina | ← | ← | ← | ← | ← | ← |
| pH | 5.0 | ← | ← | ← | ← | ← | ← |
| Temperature | 50° C. | ← | ← | ← | ← | ← | ← |
| Time | 1 h | 2 h | 3 h | 5 h | 10 h | 24 h | ← |
| Treatment pressure | 100 MPa | ← | ← | ← | ← | ← | 50 MPa |
| Disruption rate (%) | 38.6 | 33.9 | 45.8 | 47.4 | 60.5 | 87.0 | 75.9 |
| Lipid yield (%) | — | — | — | — | — | 69 | 70 |

TABLE 2

|  | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Comp. Ex. 10 | Comp. Ex. 11 | Comp. Ex. 12 | Comp. Ex. 13 |
|---|---|---|---|---|---|---|---|---|---|---|---|---|---|
| Algal body | N. salina | ← | ← | ← | ← | ← | ← | ← | ← | ← | ← | ← | ← |
| pH | 7.3 | 5.0 | ← | ← | ← | ← | ← | ← | ← | ← | ← | ← | ← |
| Temperature | 25° C. | ← | ← | ← | ← | ← | ← | 80° C. | ← | ← | ← | ← | 50° C.(2) |
| Time | 0 h(1) | 0 h(1) | 1 h | 2 h | 3 h | 10 h | 24 h | 1 h | 2 h | 3 h | 10 h | 24 h | 24 h(2) |

TABLE 2-continued

|  | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Comp. Ex. 10 | Comp. Ex. 11 | Comp. Ex. 12 | Comp. Ex. 13 |
|---|---|---|---|---|---|---|---|---|---|---|---|---|---|
| Treatment pressure | 100 MPa | ← | ← | ← | ← | ← | ← | ← | ← | ← | ← | ← | ← |
| Disruption rate (%) | 16.9 | 18.7 | 16.1 | 11.9 | 13.2 | 18.5 | 16.1 | 21.8 | 18.5 | 24.8 | 18.5 | 23.0 | 19.3 |
| Lipid yield (%) | — | 6 | — | — | — | — | — | — | — | — | — | — | — |

[1]A sample solution with a predetermined algal concentration and predetermined pH obtained at room temperature was physically treated within 30 minutes without performing any thermal treatment.
[2]Thermal treatment was performed after the disruption process.

TABLE 3

|  | Example 8 | Example 9 | Example 10 | Example 11 | Comp. Ex. 14 | Comp. Ex. 15 | Comp. Ex. 16 | Comp. Ex. 17 |
|---|---|---|---|---|---|---|---|---|
| Algal body | N. salina | ← | ← | ← | ← | ← | ← | ← |
| pH | 5.0 | ← | ← | ← | ← | ← | ← | ← |
| Temperature | 40° C. | 45° C. | 55° C. | 60° C. | 4° C. | 37° C. | 70° C. | 80° C. |
| Time | 24 h | ← | ← | ← | ← | ← | ← | ← |
| Treatment pressure | 100 MPa | ← | ← | ← | ← | ← | ← | ← |
| Disruption rate (%) | 49.5 | 92.0 | 81.2 | 72.1 | 19.9 | 19.0 | 29.4 | 23.0 |
| Lipid yield (%) | 33 | 74 | 73 | 55 | — | — | — | — |

Example 12

The disruption process was performed in the same manner as Example 1 except that the pH of the treatment solution was adjusted to 4.0 at 25° C. with 1 M HCl and the thermal treatment was performed for 10 hours. The cell disruption rate was 40.3%.

Example 13

The disruption process was performed in the same manner as Example 12 except that the thermal treatment was performed for 24 hours. The cell disruption rate was 66.0%.

Example 14

The disruption process was performed in the same manner as Example 1 except that the pH of the treatment solution was adjusted to 6.8 at 25° C. and the thermal treatment was performed for 24 hours. The cell disruption rate was 53.5%.

Example 15

The disruption process was performed in the same manner as Example 1 except that the pH of the treatment solution at 25° C. was not adjusted and maintained at 7.3 and the thermal treatment was performed for 24 hours. The cell disruption rate was 52.3%.

Example 16

The disruption process was performed in the same manner as Example 15 except that the thermal treatment was performed for 48 hours. The cell disruption rate was 66.6%.

Example 17

The disruption process was performed in the same manner as Example 1 except that the pH of the treatment solution was adjusted to 9.0 at 25° C. with 1 M NaOH and the thermal treatment was performed for 24 hours. The cell disruption rate was 47.4%.

Comparative Example 18

The disruption process was performed in the same manner as Example 1 except that the pH of the treatment solution was adjusted to 2.0 at 25° C. with 1 M HCl and the thermal treatment was performed for 24 hours. The cell disruption rate was 23.6%.

Comparative Example 19

The disruption process was performed in the same manner as Example 1 except that the pH of the treatment solution was adjusted to 3.0 at 25° C. with 1 M HCl and the thermal treatment was performed for 24 hours. The cell disruption rate was 16.0%.

Comparative Example 20

The disruption process was performed in the same manner as Example 1 except that the pH of the treatment solution was adjusted to 10.0 at 25° C. with 1 M NaOH and the thermal treatment was performed for 24 hours. The cell disruption rate was 26.5%.

Comparative Example 21

The disruption process was performed in the same manner as Example 1 except that the pH of the treatment solution was adjusted to 12.0 at 25° C. with 1 M NaOH and the thermal treatment was performed for 24 hours. The cell disruption rate was 18.6%.

Table 4 collectively shows the conditions and cell disruption rates of Examples 12-17 and Comparative Examples 18-21.

TABLE 4

|  | Example 12 | Example 13 | Example 14 | Example 15 | Example 16 | Comp. Ex. 18 | Comp. Ex. 19 | Comp. Ex. 20 | Comp. Ex. 21 |
| --- | --- | --- | --- | --- | --- | --- | --- | --- | --- |
| Algae body | N. salina | ← | ← | ← | ← | ← | ← | ← | ← |
| pH | 4.0 | ← | 7.3 | ← | 9.0 | 2.0 | 3.0 | 10.0 | 12.0 |
| Temperature | 50° C. | ← | ← | ← | ← | ← | ← | ← | ← |
| Time | 10 h | 24 h | 24 h | 48 h | 24 h | 24 h | 24 h | 24 h | 24 h |
| Treatment pressure | 100 MPa | ← | ← | ← | ← | ← | ← | ← | ← |
| Disruption rate (%) | 40.3 | 66.0 | 52.3 | 66.6 | 47.4 | 23.6 | 16.0 | 26.5 | 18.6 |

Example 18

As the microalgae belonging to Heterokontophyta, *Nannochloropsis oculata* "Chilled Nanno Yanmarine K-1" (Chlorella Industry Co. Ltd., liquid comprising the treatment solution: seawater, algal concentration: 50 g/L) was used after being warmed up to room temperature. Further, the treatment solution was diluted with artificial seawater (Daigo's artificial seawater SP for Marine Microalgae Medium, Nihon Pharmaceutical Co., Ltd.) to have an algal concentration of 1.0 g/L. The treatment solution had a pH of 5.0 at 25° C. The treatment solution thus prepared was subjected to a disruption process performed in the same manner as Example 1 except that the thermal treatment was performed for 5 hours. The cell disruption rate was 47.4%.

Example 19

The disruption process was performed in the same manner as Example 18 except that the thermal treatment was performed for 10 hours. The cell disruption rate was 49.4%.

Comparative Example 22

The disruption process was performed in the same manner as Example 18 except that neither the pH adjustment nor the thermal treatment was performed. Specifically, a treatment solution of *Nannochloropsis oculata* "Chilled Nanno Yanmarine K-1" (algal concentration: 1.0 g/L), the pH of which was maintained at 6.8 at 25° C., was physically treated using the high pressure dispersion apparatus within 30 minutes after the dilution without performing any thermal treatment. The cell disruption rate was 19.6%.

Comparative Example 23

The disruption process was performed in the same manner as Example 18 except that the thermal treatment was performed at 25° C. for 10 hours. The cell disruption rate was 22.7%.

Table 5 collectively shows the conditions and cell disruption rates of Examples 18-19 and Comparative Examples 22-23.

TABLE 5

|  | Example 17 | Example 18 | Comparative Example 22 | Comparative Example 23 |
| --- | --- | --- | --- | --- |
| Algal body | N. oculata | ← | ← | ← |
| pH | 5.0 | ← | 6.8 | 5.0 |
| Temperature | 50° C. | ← | 25° C. | ← |
| Time | 5 h | 10 h | 0 h[1] | 10 h |
| Disruption rate (%) | 47.4 | 49.4 | 19.6 | 22.7 |

[1]A sample solution with a predetermined algal concentration and predetermined pH obtained at room temperature was physically treated within 30 minutes without performing any thermal treatment.

Example 20

As the microalgae belonging to Heterokontophyta, *Nannochloropsis sauna* (liquid comprising the treatment solution: artificial seawater (Daigo's artificial seawater SP, Nihon Pharmaceutical Co., Ltd., algal concentration: 1.0 g/L)) was used. The treatment solution had a pH of 7.3. To this treatment solution, 1 M HCl was dropped to adjust the pH of the treatment solution to 6.3 at 25° C. Then, aluminum sulfate (Central Glass Co., Ltd., trade name: "Sulfate Band") was added to a concentration of 0.1% relative to the treatment solution, and stirred for 5 minutes. After the stirring was stopped, the obtained solution was left stand at room temperature for 3 hours. During this period, the algal bodies were coagulated and precipitated. Thereafter, the supernatant was partially disposed to control the algal concentration to 15.2 g/L. The pH of the treatment solution was adjusted to 5.0 at 25° C. by dropping 1 M HCl. The solution with the pH thus adjusted was thermally treated. The thermal treatment was performed at 50° C. for 24 hours. After the thermal treatment, a physical treatment was performed using a pressure homogenizer at an inlet pressure of 100 MPa. The cell disruption rate was 77.6%.

DESCRIPTION OF REFERENCE CHARACTERS

100 Homogenizing Valve
101 Homogenizing Valve Seat
102 Homogenizing Valve Body
103 Impact Ring
110 Chamber
111 Inflow Duct
112 Shear Duct
113 Outflow Duct
120 Chamber
121 Inflow Duct
122 Shear Duct
123 Outflow Duct

The invention claimed is:

1. A method for algae disruption, comprising: a thermal treatment of microalgae belonging to Heterokontophyta at a pH in the range 3.5 through 9.5 and at a temperature in the range 40° C. through 65° C.; and a physical treatment of the microalgae using a high pressure dispersion apparatus, the physical treatment following the thermal treatment, wherein the thermal treatment is performed for 3 hours or more.

2. The method for algae disruption of claim 1, wherein the microalgae are of the genus *Nannochloropsis*.

3. The method for algae disruption of claim 2, wherein the genus *Nannochloropsis* is one or more selected from the group consisting of *Nannochloropsis oculata*, *Nannochloropsis salina*, and *Nannochloropsis gaditana*.

4. The method for algae disruption of claim 1, wherein the thermal treatment is performed at a pH in the range 5.0 through 7.5.

5. The method for algae disruption of claim 1, wherein the thermal treatment is performed for 10 hours or more.

6. The method for algae disruption of claim 1, wherein the thermal treatment is performed for 20 hours or more.

7. The method for algae disruption of claim 1, wherein the thermal treatment is performed at a temperature in the range 45° C. through 60° C.

8. The method for algae disruption of claim 1, wherein the thermal treatment is performed at a temperature in the range 45° C. through 55° C.

9. The method for algae disruption of claim 1, wherein the thermal treatment is performed at a pH in the range 5.0 through 7.5 and a temperature in the range 45° C. through 60° C. for 10 hours or more.

10. The method for algae disruption of claim 1, wherein the thermal treatment is performed without adding an enzyme which decomposes a cell wall.

11. The method for algae disruption of claim 1, wherein the high pressure dispersion apparatus is a homogenizing valve-type high pressure dispersion apparatus, or a chamber-type high pressure dispersion apparatus.

12. The method for algae disruption of claim 1 further comprising recovering lipids from the disrupted algae following the thermal and physical treatments.

13. The method for algae disruption of claim 12, wherein the recovery of the lipid is performed by one or a combination of two or more of solvent extraction, centrifugation, standing, and column chromatography.

14. The method for algae disruption of claim 13, wherein a nonpolar solvent is used for the solvent extraction for the recovery of the lipid.

15. The method for algae disruption of claim 13, wherein the solvent extraction for the recovery of the lipid is performed at a temperature in the range 10° C. through 60° C.

* * * * *